United States Patent
Schrott

(10) Patent No.: US 9,364,420 B2
(45) Date of Patent: Jun. 14, 2016

(54) HAIR CONDITIONING COMPOSITIONS

(71) Applicant: Adam Patrick Schrott, Cincinnati, OH (US)

(72) Inventor: Adam Patrick Schrott, Cincinnati, OH (US)

(73) Assignee: Kao USA Inc., Cincinnati, OH (US)

( * ) Notice: Subject to any disclaimer, the term of this patent is extended or adjusted under 35 U.S.C. 154(b) by 36 days.

(21) Appl. No.: 13/746,575

(22) Filed: Jan. 22, 2013

(65) Prior Publication Data

US 2013/0164240 A1     Jun. 27, 2013

Related U.S. Application Data

(63) Continuation-in-part of application No. 13/208,796, filed on Aug. 12, 2011, now abandoned.

(60) Provisional application No. 61/374,829, filed on Aug. 18, 2010.

(51) Int. Cl.

| | | |
|---|---|---|
| *A61K 8/893* | (2006.01) | |
| *A61K 8/891* | (2006.01) | |
| *A61K 8/33* | (2006.01) | |
| *A61K 8/34* | (2006.01) | |
| *A61K 8/37* | (2006.01) | |
| *A61Q 5/00* | (2006.01) | |
| *A61Q 5/12* | (2006.01) | |
| *A61K 8/81* | (2006.01) | |
| *A61K 8/898* | (2006.01) | |
| *A61Q 5/04* | (2006.01) | |
| *A61Q 5/06* | (2006.01) | |

(52) U.S. Cl.
CPC . *A61K 8/893* (2013.01); *A61K 8/33* (2013.01); *A61K 8/342* (2013.01); *A61K 8/37* (2013.01); *A61K 8/8111* (2013.01); *A61K 8/891* (2013.01); *A61K 8/898* (2013.01); *A61Q 5/00* (2013.01); *A61Q 5/12* (2013.01); *A61Q 5/04* (2013.01); *A61Q 5/06* (2013.01)

(58) Field of Classification Search
CPC ............ A61K 8/37; A61K 8/898; A61K 8/06
See application file for complete search history.

(56) References Cited

U.S. PATENT DOCUMENTS

| | | | |
|---|---|---|---|
| 8,865,145 B2 * | 10/2014 | Molenda et al. | 424/70.12 |
| 2001/0055577 A1 * | 12/2001 | Ueyama et al. | 424/70.1 |
| 2006/0024258 A1 * | 2/2006 | Fack et al. | 424/70.4 |
| 2011/0123563 A1 * | 5/2011 | Langella et al. | 424/195.18 |
| 2011/0189248 A1 * | 8/2011 | Baldaro et al. | 424/401 |

FOREIGN PATENT DOCUMENTS

| | | | |
|---|---|---|---|
| EP | 2186543 A1 * | 5/2010 | |
| WO | WO 2010057615 A1 * | 5/2010 | |

OTHER PUBLICATIONS

Thornley Company, (Thorcosil, The silicone advantage!, Jul. 2009, pp. 1-8).*

* cited by examiner

*Primary Examiner* — Sean Basquill
*Assistant Examiner* — Mark V Stevens
(74) *Attorney, Agent, or Firm* — Frost Brown Todd LLC

(57) ABSTRACT

Compositions for providing hair care benefits, such as smoothing, anti-static control, color protection, frizz control and moisturization are disclosed. The compositions maintain clarity, show no separation upon standing, and remain flowable liquids at room temperature. The compositions comprise a premix consisting essentially of (a) siloxane polymers containing one or more functional groups selected from amino, phenyl, methoxy, hydroxyl, fatty alcohol, fatty acid, alkyl and combinations thereof; and (b) materials selected from dimethicones having a viscosity of from about 20 to about 10,000 centipoise, mono-esters containing 20 or fewer carbon atoms, ethers containing 20 or fewer carbon atoms, linear or branched hydrocarbons containing 12 to 20 carbon atoms, and combinations thereof. The compositions can be applied directly to hair (i.e., "neat") or via conventional hair treatment compositions, such as shampoos or conditioners.

6 Claims, No Drawings

HAIR CONDITIONING COMPOSITIONS

This application is a continuation in part of U.S. patent application Ser. No. 13/208,796, filed Aug. 12, 2011, which is related to and claims priority from U.S. Provisional Patent Application No. 61/374,829, filed Aug. 18, 2010, both applications being incorporated herein by reference.

BACKGROUND

Non-volatile silicones and non-volatile hydrocarbons are known in the art to provide a number of consumer recognized hair care benefits, such as smoothing, static control, color protection, fizz control and moisturization. However, those materials are very difficult to deliver in a consumer acceptable or efficacious manner to the hair in their concentrated form or when they are added to a formulation in their concentrated form.

Current technology utilizes volatile cyclic siloxanes, volatile linear siloxanes or volatile hydrocarbons as carriers for high viscosity linear polydimethylsiloxane (PDMS) materials or non-volatile hydrocarbons. These materials can have a number of undesirable attributes as carriers. Specifically, they may not be cost effective, they do not provide the best vehicle for delivery of the high viscosity PDMS (as seen by decreased performance in terms of the above-mentioned attributes), and they are currently regulated or under increased scrutiny by governmental health and environmental organizations. Current compositions utilize high viscosity polydimethylsiloxanes in volatile compounds, such as cyclopentasiloxane, cyclomethicone, low molecular weight polydimethylsiloxanes, or low molecular weight hydrocarbons, such as isododecane or isoparaffins. While these compositions may be the best available, they are not particularly effective in delivering the benefits which can be provided by these high viscosity PDMS materials.

Thus, there is a recognized need to find a delivery system which is useful for delivering the hair care benefits of high viscosity linear polydimethylsiloxane materials and non-volatile hydrocarbons. That is the focus of the present invention. Specifically, the present invention provides hair conditioning compositions, incorporating high viscosity non-volatile silicone and hydrocarbon materials, which may be delivered "neat" for applications such as, but not limited to, hair serums and hair shine sprays, or may be added as a "premix" to known hair care compositions, such as conditioners, styling creams, hair lotions, hair moisturizers, hair colors, permanent wave compositions or styling gels, in order to effectively deliver the benefits which are seen with such materials. Additionally, the compositions of the present invention maintain clarity and show no separation upon standing, remaining a flowable liquid at room temperature.

SUMMARY

The present invention relates to hair conditioning compositions which comprise a premix consisting essentially of: (a) siloxane polymers containing one or more types of functional groups selected from
(i) amino, (ii) phenyl, (iii) methoxy, (iv) hydroxyl, (v) fatty alcohol, (vi) fatty acid, and (vii) alkyl; and (b) a material selected from (i) dimethicones having a viscosity of from about 20 to about 10,000 centipoise), (ii) mono-esters containing 20 or fewer carbon atoms (iii) ethers containing 20 or fewer carbon atoms, (iv) linear or branched hydrocarbons containing 12 to 20 carbon atoms, and (v) mixtures thereof.

Hair conditioning compositions containing those defined mixtures are also claimed. The method of utilizing those mixtures to provide hair conditioning benefits when applied "neat" from a conditioning composition are also claimed. In addition, the method of making those hair conditioning compositions is also claimed.

All ratios stated herein are "by weight", unless otherwise specified. Further, all documents cited in this application are incorporated herein by reference in their entirety.

DETAILED DESCRIPTION

The present invention relates to hair conditioning compositions which comprise a premix which consists essentially of (a) one or more siloxane polymers containing specified functional groups, together with (b) a material selected from dimethicones, mono-esters containing 20 or fewer carbon atoms, ethers containing 20 or fewer carbon atoms, linear or branched hydrocarbons containing 12 to 20 carbon atoms, and mixtures of those materials. The compositions can be applied "neat" directly to hair, or can be applied as part of conventional hair conditioning compositions, such as shampoos, conditioners, styling creams, hair lotions, hair moisturizers, hair colors, permanent wave compositions, or styling gels. The compositions of the present invention maintain clarity, show minimal (if any) separation upon standing, and remain flowable liquids at room temperature. This stands in contrast to prior art siloxane-containing compositions which tend to show haziness, cloudiness and separation upon standing.

The first component utilized in the premix compositions of the present invention includes siloxane polymers containing one or more types of functional groups selected from (i) amino, (ii) phenyl, (iii) methoxy, (iv) hydroxyl, (v) fatty alcohol, (vi) fatty acid, and (vii) alkyl. Siloxanes (silicone polymers) are well-known in the art. The siloxane polymers which include the listed moieties are macromolecules comprised of a polymer backbone of alternating silicon and oxygen atoms (siloxane bonds) including the listed organic side groups, such as phenyl, amino, methoxy, hydroxyl, fatty alcohol, fatty acid, or alkyl. The number of repeating siloxane units can range from one to several thousand. By adjusting of the —Si—O-chain lengths, the functionality of the side groups and the crosslinking between molecular chains, silicones can be synthesized into an almost infinite variety of materials each with unique chemical properties and performance characteristics. Siloxane polymers are well-known in the art and their properties and synthesis are described in *Silicones and Silicone-Modified Materials*, Clarson, S. et al (see Chapter 1, *Overview of Siloxane Polymers*, by James E. Mark), ACS Symposium Series, American Chemical Society, Washington, D.C., 2000, incorporated herein by reference. The siloxane materials utilized in the present premix compositions are selected from those containing amino groups, phenyl groups, methoxy groups, hydroxyl groups, fatty alcohol groups, fatty acid groups, alkyl groups, or combination of those moieties. Examples of specific siloxane polymers which can be utilized in the present compositions include amodimethicone, bis-cetearyl amodimethicone, bis-stearyldimethicone, bis-hydroxy/methoxy amodimethicone, stearyldimethicone, and aminopropyl phenyl trimethicone. Mixtures of these polymers can be used.

The second component utilized in the premix compositions of the present invention include a material selected from dimethicones having a viscosity of from about 20 to about 10,000 centipoise; monoesters containing 20 or fewer carbon atoms; ethers containing 20 or fewer carbon atoms; linear or branched chain hydrocarbons containing 12 to 20 carbon atoms; and combinations of those materials. Such materials are well-known in the art. For example, dimethicones are siloxane materials (as described above) wherein each silicon atom includes 2 methyl side chains; the viscosity of those dimethicone materials must be from about 20 to about 10,000 centipoise in order to be useful in the premixes of the present invention. Examples of monoesters containing 20 or fewer carbon atoms useful in the present invention include isodecyl neopentanoate, isodecyl isononanoate, isononyl isononanoate, tridecyl neopentanoate, and combinations of those materials. Examples of linear ether materials containing 20 or fewer carbon atoms useful in the present invention include dicaprylyl ether, diisononyl ether, didecyl ether, and combinations of those materials.

The siloxane polymer materials are generally used at levels of from about 5% to about 25%, for example from about 10% to about 20%, by weight, of the premix composition. The second component of the mixture (i.e., the dimethicone/monoester/ether/hydrocarbon component) is generally used at levels from about 75% to about 95%, for example from about 80% to about 90%, by weight, of the premix composition. Specific examples of these premixtures are set forth in the following Tables.

The premixtures are made by taking the siloxane polymer and the second component, defined above, and premixing them prior to their being mixed with the remaining components utilized in the hair conditioning compositions defined herein. Such premixture can be accomplished by conventional means, for example, the siloxane polymer and the second component can be combined in a vessel and mixed with sufficient shear until homogeneous. Heat may be applied, if needed.

TABLE 1(A)

Pre-Mix Formulation (wt/wt %)

| Material | 1 | 2 | 3 | 4 | 5 | 6 | 7 | 8 | 9 | 10 | 11 |
|---|---|---|---|---|---|---|---|---|---|---|---|
| Isodecyl Neopentanoate | 85 | 75 | — | — | — | — | — | — | — | — | — |
| Isodecyl Isononanoate | — | — | 85 | — | — | — | — | — | — | — | — |
| Isononyl Isononanoate | — | — | — | 80 | — | — | — | — | — | — | — |
| Tridecyl Neopentanoate | — | — | — | — | 85 | — | — | — | — | — | — |
| Dicaprylyl Ether | — | — | — | — | — | 90 | — | — | — | — | — |
| Diisononyl Ether | — | — | — | — | — | — | 85 | — | — | — | — |
| Didecyl Ether | — | — | — | — | — | — | — | 85 | — | — | — |
| Dimethicone (250 cs) | — | — | — | — | — | — | — | — | 80 | — | — |
| Dimethicone (5,000 cs) | — | — | — | — | — | — | — | — | — | 75 | — |
| Dimethicone (10,000 cs) | — | — | — | — | — | — | — | — | — | — | 85 |
| Amodimethicone | — | 25 | — | — | — | 10 | 15 | — | — | — | — |
| Bis-Cetearyl Amodimethicone | 15 | — | — | — | — | — | — | — | — | 25 | — |
| Bis-Stearyl Dimethicone | — | — | — | 20 | — | — | — | — | — | — | — |
| Bis-Hydroxy/Methoxy Amodimethicone | — | — | 15 | — | — | — | — | 15 | 20 | — | — |
| Stearyl Dimethicone | — | — | — | — | — | — | — | — | — | — | 15 |
| Amino Phenyl Trimethicone | — | — | — | — | 15 | — | — | — | — | — | — |

TABLE 1(B)

Pre-Mix Formulation (wt/wt %)

| Material | 12 | 13 | 14 | 15 | 16 | 17 | 18 | 19 | 20 | 21 | 22 |
|---|---|---|---|---|---|---|---|---|---|---|---|
| Isodecyl Neopentanoate | 85 | 75 | — | — | — | — | — | — | — | — | — |
| Isodecyl Isononanoate | — | — | 85 | — | — | — | — | — | — | — | — |
| Isononyl Isononanoate | — | — | — | 80 | — | — | — | — | — | — | — |
| Tridecyl Neopentanoate | — | — | — | — | 85 | — | — | — | — | — | — |
| Dicaprylyl Ether | — | — | — | — | — | 90 | — | — | — | — | — |
| Diisononyl Ether | — | — | — | — | — | — | 85 | — | — | — | — |
| Didecyl Ether | — | — | — | — | — | — | — | 85 | — | — | — |
| Dimethicone (250 cs) | — | — | — | — | — | — | — | — | 80 | — | — |
| Dimethicone (5,000 cs) | — | — | — | — | — | — | — | — | — | 75 | — |
| Dimethicone (10,000 cs) | — | — | — | — | — | — | — | — | — | — | 85 |
| Amodimethicone | — | — | 15 | — | 15 | — | — | — | — | — | — |
| Bis-Cetearyl Amodimethicone | — | — | — | — | — | — | — | — | 20 | — | — |
| Bis-Stearyl Dimethicone | — | 25 | — | — | — | 10 | — | — | — | — | — |
| Bis-Hydroxy/Methoxy Amodimethicone | 15 | — | — | — | — | — | — | — | — | 25 | 15 |
| Stearyl Dimethicone | — | — | — | 20 | — | — | — | 15 | — | — | — |
| Amino Phenyl Trimethicone | — | — | — | — | — | — | 15 | — | — | — | — |

The premix compositions, as defined above, may be applied directly to hair (i.e., "neat" application) such as from a hair serum or a hair shine spray, or they may be applied from more complete hair conditioning compositions. Such compositions include, but are not limited to, shampoos, conditioners, styling creams, hair lotions, hair moisturizers, hair coloring compositions, permanent wave compositions and styling gels. These compositions are well-known to those skilled in the art; for example, shampoo compositions are described in U.S. Pat. No. 6,706,258, Gallagher et al, issued Mar. 16, 2004, incorporated herein by reference.

The hair conditioning compositions typically comprise from about 0.5% to about 15%, for example, from about 0.5% to about 5%, of the premix composition. Embodiments of the hair conditioning compositions of the present invention may additionally comprise from about 0.5% to about 15% fatty alcohol; and/or from about 0.2% to about 12% of an emulsifier suitable for use in hair care compositions; and/or from about 5% to about 98.5% water.

Emulsifiers suitable for use in the compositions of the present invention are well-known in the art and are those which are suitable for use in hair care compositions. Specifically, they are ones which are compatible with the remaining components of the hair care composition and which are suitable for application to hair and scalp. Examples of such emulsifiers include cationic surfactants, nonionic surfactants, amine salts and mixtures of those materials. Emulsifiers are surfactants used to stabilize emulsions (droplets of oil-in-water) in hair care products. Generally an emulsifier is an organic compound that incorporates within the same molecule two dissimilar structural groups, e.g., a water-soluble and a water-insoluble moiety. It is the ingredient which bonds together the water and oil in a cream or lotion. The composition, solubility properties, location and relative sizes of these dissimilar groups in relation to the overall molecular configuration determine the surface activity (emulsification ability) of a compound.

Emulsifiers are classified on the basis of their hydrophilic or solubilizing groups into four categories: anionic, nonionic, cationic and amphoteric. Cationic surfactants, nonionic surfactants, and amine salts are examples of emulsifiers useful in the present invention. An example of a nonionic emulsifier is a polyoxyethylene surfactant, such as ethoxylated alkyl phenols, ethoxylated aliphatic alcohols, glycerol esters, polyoxyethylene glycerol esters, glycol esters of fatty acids, and ethoxylated natural fats, oils and waxes. Examples of amine salt emulsifiers include salts of fatty amine oxides, polyoxyethylene alkyl and alicyclic amines, and mono-alkyl olamides. Examples of cationic emulsifiers utilized in the present compositions include mono-, di- or tri-alkyl quaternary ammonium or imidazolinium materials. These emulsifiers are well-known in the art and, for example, are described at length in *The Complete Book On Emulsifiers With Uses, Formulae Processes*, NPCS Board of Consultants & Engineers. Examples of additional emulsifiers which can be used in hair care compositions include $C_{14}$-$C_{16}$ glycol palmitate, $C_{18}$-$C_{20}$ glycol isostearate, ceteareth (4-60), cocamidopropyl lauryl ether, deceth (3-10), dipentaerythritol hydroxystearate, dodoxynol (5, 6, 7, 9, 12), octoxynol (1-70), palm kernel glycerides, behentrimonium chloride, distearyl dimonium chloride, Quaternium-91, behenamidopropyl dimethylamine lactate, and mixtures thereof.

The hair conditioning compositions of the present invention can additionally include from about 0.5% to about 15% of a fatty alcohol material. Fatty alcohols are aliphatic alcohols, usually consisting of a chain of 8 to 22 carbon atoms, but can include up to 36 or even more carbon atoms. Fatty alcohols usually have an even number of carbon atoms and a single alcohol group (—OH) attached to the terminal carbon. Some fatty alcohols are unsaturated and some are branched chain. The traditional and still important source of fatty alcohols are fatty acid esters. Wax esters were formerly extracted from sperm oil, obtained from whales. An alternative plant source is jojoba. Fatty acid triesters, known as triglycerides, are obtained from plant and animal sources. These triesters are subjected to transesterification to give methylesters, which in turn are hydrogenated to form the alcohols. Although tallow is typically $C_{16}$-$C_{18}$, the chain length from plant sources are more variable. Higher alcohols ($C_{20}$-$C_{22}$) can be obtained from rapeseed. Shorter alcohols ($C_{12}$-$C_{14}$) are obtained from coconut oil. Fatty alcohols are also prepared from petrochemical sources. In the Ziegler process, ethylene is oligomerized using triethyl aluminum followed by air oxidation. Alternatively, ethylene can be oligomerized to provide mixtures of alkenes, which are subjected to hydroformylation, providing odd numbered aldehydes, which can subsequently be hydrogenated. Examples of fatty alcohols include lauryl alcohol (1-dodecanol; 12 carbon atoms), myristyl alcohol (1-tetradecanol; 14 carbon atoms), cetyl alcohol (1-hexadecanol; 16 carbon atoms), stearyl alcohol (1-octodecanol; 18 carbon atoms), oleyl alcohol (cis-9-octadecen-1-ol; 18 carbon atoms, unsaturated), behenyl alcohol (1-docosanol, 22 carbon atoms), erucyl alcohol (cis-13-docosen-1-ol; 22 carbon atoms, unsaturated), and cetearyl alcohol which is a mixture of fatty alcohols, consisting predominantly of cetyl and stearyl alcohols.

If the compositions are formulated into shampoos, such compositions can comprise one or more cleaning surfactants which are cosmetically acceptable and suitable for topical application to the hair. Suitable surfactants, which may be used singularly or in combination, are selected from anionic, amphoteric and zwitterionic surfactants, and mixtures of those materials. Examples of anionic surfactant include alkyl sulfates, alkyl ether sulfates, alkaryl sulfonates, alkanoyl isethionates, alkyl succinates, alkyl sulfosuccinates, alkyl sarcosinates, alkyl phosphates, alkyl ether phosphates, alkyl ether carboxylates, and alpha-olefin sulfonates, especially their sodium, magnesium, ammonium, and mono-, di- and triethanolamine salts. The alkyl and acyl groups in these materials contain generally from 8 to 18 carbon atoms and may be unsaturated. The alkyl ether sulfates, alkyl ether phosphates and alkyl ether carboxylates generally contain from 1 to 10 ethylene oxide or propylene oxide units per molecule.

Typical anionic surfactants for use in shampoos include sodium oleyl succinate, ammonium lauryl sulfosuccinate, ammonium lauryl sulfate, sodium dodecylbenzene sulfonate, triethanolamine dodecylbenzene sulfonate, sodium cocoyl isethionate, sodium lauryl isethionate and sodium n-lauroyl sarcosinate. Examples of anionic surfactants include sodium lauroyl sulfate, triethanolamine monolauroyl phosphate, sodium lauroyl ether sulfate (1 EO, 2 EO and 3 EO), ammonium lauroyl sulfate and ammonium lauroyl ether sulfate (1 EO, 2 EO) and 3 EO).

Examples of amphoteric and zwitterionic surfactants include alkyl amine oxides, alkyl betaines, alkyl amidopropyl betaines, alkyl sulfobetaines (sultaines), alkyl glycinates, alkyl carboxyglycinates, alkyl amphopropionates, alkyl amphoglycinates, alkyl amidopropyl hydroxyl sultaines, acyl taurates and acyl glutamates, wherein the alkyl and acyl groups contain from 8 to 19 carbon atoms. Typical amphoteric and zwitterionic surfactants for use in shampoos include lauryl amine oxide, cocadimethyl amine oxide, sulfopropyl betaine, lauryl betaine, cocamidopropyl betaine and sodium cocamidopropionate.

The shampoo compositions may additional contain cationic deposition enhancing polymers, non-silicone conditioning agents, antimicrobial agents, and aesthetic agents, such as colorants, fragrances, naturally derived materials (such as plant extracts), and pearlescing agents. Other components which may be used include viscosity modifiers, preservatives, polyols (such as glycerin and polypropylene glycol), chelating agents (such as EDTA), antioxidants, sunscreens, and carriers (which can be, for example, ethanol and/or water).

Hair conditioning compositions are also well-known in the art. For example, they are described in U.S. Pat. No. 6,287,545, Su, issued Sep. 11, 2001, incorporated herein by reference. Such hair conditioner compositions commonly include long chain mono-, di- or even tri-higher alkyl quaternary ammonium compounds (such cetyl trimonium chloride), fatty alcohols (such as cetyl alcohol or stearyl alcohol), mineral oil, humectants, surfactants/emulsifiers, thickeners (such as cellulose derivatives), polycationic polymers (known as polyquaterniums), colorants, perfumes, opacifiers, pearlescent aides, buffers, preservatives, antioxidants, and carriers (which can be, for example, ethanol and/or water).

Examples of conditioner formulations, in general terms, which include the binary premix compositions of the present invention are set forth in the following table:

TABLE 2

General Examples of Conditioner Formulations

| General Material Description | General wt/wt % |
|---|---|
| Choose from Lactic, Malic, Tartaric, Fumaric, Isononanoic, Citric, Succinic, Gluconic, and/or Salicylic Acids | 0.2-0.6 |
| C16-18 Fatty Alcohol | 4.0-6.0 |
| Ester | 0.2-0.4 |
| Alkylamidoamine | 1.0-2.0 |

TABLE 2-continued

General Examples of Conditioner Formulations

| General Material Description | General wt/wt % |
|---|---|
| "Neat" Formulation #X (see Tables 1A and 1B) | 0.75-3.0 |
| Preservative | as appropriate |
| Fragrance | as appropriate |
| Carrier | Balance |

Examples of other types of hair care products, including hair styling products, are taught, for example, in U.S. Pat. No. 7,850,952, Ivanova et al, issued Dec. 14, 2010; U.S. Pat. No. 7,785,575, Anderson et al, issued Aug. 31, 2010; U.S. Pat. No. 6,586,378, Chandra, issued Jul. 1, 2003; and U.S. Pat. No. 6,136,296, Midha et al, issued Oct. 24, 2000, all of which are incorporated herein by reference.

When utilized as described herein, the compositions of the present invention are applied in an "effective amount", i.e., an amount which provides the hair conditioning and/or moisturizing benefits desired, but not so much as to result in undesirable effects to the user (e.g., greasiness to the hair or adverse scalp or skin reactions).

Examples of compositions of the present invention are set forth below. They are intended to be merely illustrative, and not limiting, of the present invention.

Examples 1-8

Conditioner formulations incorporating the binary mixtures of the present invention contain the following components and are prepared using conventional techniques:

| | | (wt/wt %) | | | | | | | |
|---|---|---|---|---|---|---|---|---|---|
| | | 1 Balance | 2 Balance | 3 Balance | 4 Balance | 5 Balance | 6 Balance | 7 Balance | 8 Balance |
| A | pH Regulator (Lactic Acid, Malic Acid, Tartaric Acid, Fumaric Acid, Isononanoic Acid, Citric Acid, Salicylic Acid, Gluconic Acid) | qs | qs | qs | qs | qs | qs | qs | qs |
| | Glycerin | | | 10.00 | | | 5.00 | | |
| B | Cetearyl Alcohol | 5.00 | 5.00 | 8.00 | 4.00 | 3.00 | 6.00 | 5.00 | 4.00 |
| | Behenamidopropyl Dimethylamine | 2.00 | 1.00 | 3.00 | | | | | |
| | Distearyldimonium Chloride | | 0.15 | | | | 0.20 | | |
| | Behentrimonium Chloride | | | | 2.00 | 3.00 | 3.00 | 2.00 | 3.00 |
| C | Tridecyl Isononanoate | 1.50 | | | | 1.80 | | | |
| | Diisononyl Ether | | 0.85 | | | 2.25 | | 1.28 | |
| | Dimeticone (5,000 cs) | | | 1.70 | | | 0.90 | | 0.80 |
| | Bis-Cetearyl Amodimethicone | 0.50 | | 0.30 | | | 0.10 | | 0.20 |
| | Bis-Hydroxy/Methoxy Amodimethicone | | 0.15 | | | 0.75 | | 0.23 | |
| | Stearyl Dimethicone | | | | 0.20 | | | | |
| D | Preservative (Choice) | qs | qs | qs | qs | qs | qs | qs | qs |
| | Fragrance | qs | qs | qs | qs | qs | qs | qs | qs |
| | Target pH | | | | 3.5-5.0 | | | | |

Example 9

Hair Shine Spray

A hair shine spray of the present invention is made as follows:

| Material | wt/wt % |
|---|---|
| Dicaprylyl Ether | 90 |
| Amodimethicone | 10 |

Add ingredients in order to main vessel with mixing. Mix until homogeneous. Using suitable package, finished composition may be applied by spraying onto hair to provide a shine benefit.

Example 10

Hair Serum

| Material | wt/wt % |
|---|---|
| Isodecyl Neopentanoate | 70 |
| Dimethicone (10,000 cs) | 5 |
| Bis-Hydroxy/Methoxy Amodimethicone | 25 |

Add ingredients in order to main vessel with mixing. Mix until homogeneous. Using suitable package, finished composition may be dispensed into the hands and then spread through the hair to provide a shine benefit.

Example 11

Hair Combing Cream

|   | Material | wt/wt % |
|---|---|---|
| A | Water | Balance |
|   | Glycerin | 7.50 |
| B | Benentrimonium Chloride | 2.00 |
|   | Cetearyl Alcohol | 4.00 |
| C | Isononyl Isononanoate | 1.70 |
|   | Aminopropyl Phenyl Trimethicone | 0.30 |
| D | Preservative | QS |
|   | Fragrance | QS |

Add ingredients in Phase (A) in order to main vessel with mixing and heating to 80 C. Mix until homogeneous. In a pre-mix vessel, add ingredients in Phase (B) with heating to 80 C with mixing. When Phase (B) is at temperature and homogeneous, slowly add to Phase (A) in main vessel. Maintain temperature and mixing until homogeneous emulsion is formed then begin cooling to 40 C. In a pre-mix vessel, add ingredients in Phase (C) in order listed with mixing until homogeneous. Once Phase (C) is homogeneous and main vessel is at 40 C, maintain vessel mixing and add Phase (C) to main vessel. Once Phase (C) has been incorporated into the emulsion, add Phase (D) ingredients in order listed with sufficient mixing to incorporate. Batch maybe homogenized with a high shear mixer if desired.

Product may be applied to the hands or comb and then spread/combed through the hair to provide a shine and conditioning benefit.

Example 12

Hair Conditioner

|   | Material | wt/wt % |
|---|---|---|
| A | Water | Balance |
|   | Gluconic Acid | (QS to pH 3.5-5.5) |
| B | Behenamidopropyl Dimethylamine | 2.00 |
|   | Cetearyl Alcohol | 4.00 |
| C | Dimethicone (250 cs) | 0.75 |
|   | Stearyl Dimethicone | 0.25 |
| D | Preservative | QS |
|   | Fragrance | QS |

Add ingredients in Phase (A) in order to main vessel with mixing and heating to 80 C. Mix until homogeneous. In a pre-mix vessel, add ingredients in Phase (B) with heating to 80 C with mixing. When Phase (B) is at temperature and homogeneous, slowly add to Phase (A) in main vessel. Maintain temperature and mixing until homogeneous emulsion is formed then begin cooling to 40 C. In a pre-mix vessel, add ingredients in Phase (C) in order listed with mixing until homogeneous. Once Phase (C) is homogeneous and main vessel is at 40 C, maintain vessel mixing and add Phase (C) to main vessel. Once Phase (C) has been incorporated into the emulsion, add Phase (D) ingredients in order listed with sufficient mixing to incorporate. Batch maybe homogenized with a high shear mixer if desired.

Composition may be applied to wet hair, spread throughout, and then rinsed with water while in the shower or bath to provide a shine and conditioning benefit.

What is claimed is:

1. A premix composition used to prepare a hair conditioner composition, said premix consisting of:
    (a) from about 5% to about 25% (by weight) of a siloxane polymer selected from amodimethicone, bis-cetearyl amodimethicone, or mixtures thereof; and
    (b) from about 75% to about 95% of a material selected from isodecyl neopentanoate, isodecyl isononoate, isononyl isononanoate, tridecyl neopentanoate, dicaprylyl ether, or mixtures thereof.

2. A hair conditioner comprising: (a) from about 0.5% to about 5% of the premix defined in claim 1; (b) from about 1% to about 2% of a material selected from an alkylamidoamine and/or a quaternary ammonium compound, and (c) the balance of the composition selected from one or more of the following components: fatty alcohols, mineral oil, humectants, surfactants/emulsifiers, thickeners, polycationic polymers, colorants, perfumes, opacifiers, pearlescent aids, buffers, preservatives, anti-oxidants, water and/or short-chain alcohols; wherein the premix components defined in (a) are mixed together prior to mixing in components (b) or (c).

3. The hair conditioner composition of claim 2 wherein the material (b) is selected from behentrimonium chloride, distearyldimonium chloride, behenamidopropyl dimethylamine, or mixtures thereof.

4. A method of manufacturing a hair conditioning composition comprising the steps of:
- (1) preparing a premix consisting of:
  - (a) siloxane polymer selected from amodimethicone, bis-cetearyl amodimethicone, or mixtures thereof; and
  - (b) material selected from isodecyl neopentanoate, isodecyl isononanoate, isononyl isononanoate, tridecyl neopentanoate, dicaprylyl ether, or mixtures thereof; and
- (2) mixing the formed premix with one or more of the following: mono-, di-, or tri-long chain quaternary ammonium or amine compounds, fatty alcohols, mineral oil, humectants, surfactants/emulsifiers, thickeners, polycationic polymers, colorants, perfumes, opacifiers, pearlescent aids, buffers, preservatives, anti-oxidants, water, and/or short-chain alcohols;
- wherein the premix consists of from about 5% to about 25% (by wt.) of component (a) and from about 75% to about 95% (by wt.) of component (b), and the composition consists of from about 0.5% to about 5% (by wt.) of the premix with the remainder being the balance defined in step (2), above.

5. The method defined in claim 4, wherein the balance defined in step (2) includes at least one material selected from: behentrimonium chloride, distearyldimonium chloride, and/or behenamidopropyl dimethylamine.

6. A method of conditioning hair consisting of applying to said hair an effective amount of the hair conditioning composition according to claim 3.

* * * * *